United States Patent
Mordaunt et al.

(10) Patent No.: US 10,076,445 B2
(45) Date of Patent: Sep. 18, 2018

(54) POSTERIO CAPSULOTOMY USING LASER TECHNIQUES

(71) Applicants: BAUSCH & LOMB INCORPORATED, Rochester, NY (US); TECHNOLAS PERFECT VISION GMBH, Munich (DE)

(72) Inventors: David Haydn Mordaunt, Los Gatos, CA (US); Frieder Loesel, Mannheim (DE); Gwillem Mosedale, Munich (DE)

(73) Assignees: BAUSCH & LOMB INCORPORATED, Rochester, NY (US); TECHNOLAS PERFECT VISION GMBH, Munich (DE)

(*) Notice: Subject to any disclaimer, the term of this patent is extended or adjusted under 35 U.S.C. 154(b) by 644 days.

(21) Appl. No.: 14/412,168

(22) PCT Filed: Mar. 14, 2013

(86) PCT No.: PCT/US2013/031394
§ 371 (c)(1),
(2) Date: Dec. 30, 2014

(87) PCT Pub. No.: WO2014/011231
PCT Pub. Date: Jan. 16, 2014

(65) Prior Publication Data
US 2015/0157507 A1 Jun. 11, 2015

Related U.S. Application Data

(60) Provisional application No. 61/671,312, filed on Jul. 13, 2012.

(51) Int. Cl.
*A61F 9/008* (2006.01)
*A61F 2/16* (2006.01)

(52) U.S. Cl.
CPC ........ *A61F 9/00834* (2013.01); *A61F 2/1662* (2013.01); *A61F 9/0081* (2013.01);
(Continued)

(58) Field of Classification Search
CPC .. A61F 9/00834; A61F 9/0084; A61F 9/0081; A61F 9/00831; A61F 2/1662;
(Continued)

(56) References Cited

U.S. PATENT DOCUMENTS

| 3,589,363 A | 6/1971 | Banko et al. |
| 3,805,787 A | 4/1974 | Banko |

(Continued)

FOREIGN PATENT DOCUMENTS

EP 0697611 A1 2/1996

OTHER PUBLICATIONS

PCT International Search Report, Application No. PCT/US2013/031394, dated Mar. 14, 2013.
(Continued)

*Primary Examiner* — John Strege
(74) *Attorney, Agent, or Firm* — Michael L. Smith

(57) ABSTRACT

A system and method are provided for removing a natural lens and inserting an Intraocular Lens (IOL) into the lens capsule of an eye. Specifically, this is accomplished by inserting the IOL through an opening on the posterior capsule that is created using a focused laser beam. The system includes a laser unit, a detector for creating images of the interior of the eye, and a computer that controls the cooperative functions of the detector and the laser unit. Based on images of the posterior capsule provided by the detector, the computer is used to control movements of the focal point through tissue of the posterior capsule to perform Laser Induced Optical Breakdown (LIOB) on posterior capsule tissue. The result is a laser capsulotomy that creates (Continued)

an opening through the posterior capsule allowing the natural lens to be removed and the IOL to be implanted.

8 Claims, 1 Drawing Sheet

(52) U.S. Cl.
CPC ........ *A61F 9/0084* (2013.01); *A61F 9/00831* (2013.01); *A61F 2009/0087* (2013.01); *A61F 2009/00851* (2013.01); *A61F 2009/00889* (2013.01)

(58) Field of Classification Search
CPC .. A61F 2009/00889; A61F 2009/00851; A61F 2009/0087
See application file for complete search history.

(56) References Cited

U.S. PATENT DOCUMENTS

| | | | |
|---|---|---|---|
| 3,941,122 A | 3/1976 | Jones | |
| 3,990,452 A | 11/1976 | Murry et al. | |
| 4,428,748 A | 1/1984 | Peyman et al. | |
| 4,531,934 A | 7/1985 | Kossovsky et al. | |
| RE31,998 E | 10/1985 | Myers | |
| 4,634,420 A | 1/1987 | Spinosa et al. | |
| 4,634,441 A | 1/1987 | Clayman et al. | |
| 4,642,114 A | 2/1987 | Rosa | |
| 4,648,878 A | 3/1987 | Kelman | |
| 4,907,586 A | 3/1990 | Bille et al. | |
| 4,955,894 A | 9/1990 | Herman | |
| 5,217,476 A * | 6/1993 | Wishinsky | A61B 17/3211 128/898 |
| 5,246,435 A | 9/1993 | Bille et al. | |
| 5,273,751 A | 12/1993 | Dubroff | |
| 5,702,441 A | 12/1997 | Zhou | |
| 5,733,276 A | 3/1998 | Belkin | |
| 5,941,887 A | 8/1999 | Steen et al. | |
| 6,030,416 A | 2/2000 | Huo et al. | |
| 6,066,138 A | 5/2000 | Sheffer et al. | |
| 6,126,629 A | 10/2000 | Perkins | |
| 6,299,591 B1 | 10/2001 | Banko | |
| 6,322,556 B1 | 11/2001 | Gwon et al. | |
| 6,325,792 B1 | 12/2001 | Swinger et al. | |
| 6,800,076 B2 | 10/2004 | Humayun | |
| 6,902,558 B2 | 6/2005 | Laks | |
| 6,913,603 B2 | 7/2005 | Knopp et al. | |
| 7,967,775 B2 | 6/2011 | Hong | |
| 8,187,168 B2 | 5/2012 | Wuchinich | |
| 2005/0234473 A1 | 10/2005 | Zacharias | |
| 2006/0195076 A1 | 8/2006 | Blumenkranz et al. | |
| 2007/0255196 A1 | 11/2007 | Wuchinich | |
| 2009/0157063 A1 * | 6/2009 | Ruiz | A61F 9/008 606/5 |
| 2010/0015562 A1 | 1/2010 | Babington | |
| 2010/0076271 A1 | 3/2010 | Humayun | |
| 2010/0082017 A1 * | 4/2010 | Zickler | A61F 9/00834 606/4 |
| 2011/0022036 A1 * | 1/2011 | Frey | A61F 9/008 606/4 |
| 2011/0022037 A1 * | 1/2011 | Bille | A61F 9/008 606/5 |
| 2011/0118609 A1 * | 5/2011 | Goldshleger | A61F 9/008 600/476 |
| 2011/0184395 A1 | 7/2011 | Schuele et al. | |
| 2011/0202044 A1 | 8/2011 | Goldshleger et al. | |
| 2011/0202046 A1 | 8/2011 | Angeley et al. | |
| 2012/0089134 A1 | 4/2012 | Horvath et al. | |
| 2013/0235341 A1 * | 9/2013 | Loesel | A61F 9/00825 351/206 |
| 2017/0246033 A1 * | 8/2017 | Bor | A61F 9/0084 |

OTHER PUBLICATIONS

Leitgeb et al., "Ultrasonic Vitrectomy—an Alternative Technique to Presently Used Mechanical Procedures," Graefes Archiv Ophthalniologie, Springer-Verlag, 1979.
Wuchinich, David, "Ultrasonic vitrectomy instrument," Ultrasonics Industry Association Symposium, 2009.

* cited by examiner

POSTERIO CAPSULOTOMY USING LASER TECHNIQUES

This application claims the benefit of U.S. Provisional Patent Application Ser. No. 61/671,312, titled POSTERIOR CAPSULOTOMY USING LASER TECHNIQUES, filed Jul. 13, 2012. The entire contents of application Ser. No. 61/671,312 are hereby incorporated by reference herein.

FIELD OF THE INVENTION

The present invention pertains generally to ocular laser surgery. More particularly, the present invention pertains to capsulotomy procedures that employ a femtosecond laser. The present invention is particularly, but not exclusively, useful for performing a posterior capsulotomy procedure to insert an Intraocular Lens (IOL) into the lens capsule of an eye.

BACKGROUND OF THE INVENTION

A common treatment for a cataract involves removal of the diseased lens from a patient's eye followed by replacement with an Intraocular Lens (IOL). Originally, the entire lens and capsule were removed and replaced. More modernly, the lens is removed from the capsule, in situ, and the new IOL is inserted into the capsule.

In a typical cataract procedure, access to the lens is obtained and the lens is fragmented and/or emulsified. For example, the lens can be emulsified using a traditional ultrasonic handpiece (a process known as "phacoemulsification"), or, more modernly, the lens can be fragmented using a femtosecond laser. Once fragmented or emulsified, the lens material can be removed from the capsule, for example, by aspirating the material using an aspiration needle. Once the lens material has been removed, an IOL can be inserted into the remaining portion of the lens capsule.

To perform the procedures described above, an opening in the lens capsule is required. Two possibilities for this opening include an anterior capsulotomy in which an opening is made on the anterior surface of the lens capsule and a posterior capsulotomy in which an opening is made on the posterior surface of the lens capsule. Typically, for an anterior capsulotomy, the surgeon gains access to the capsule and lens through incisions that are made on the cornea or limbus. However, these incisions can adversely affect the refractive properties of the eye, including the inducement of undesirable astigmatism.

Another drawback associated with a typical anterior capsulotomy procedure involves anatomical considerations. In more detail, access to the anterior capsule surface necessarily involves transit through the relatively small anterior chamber of the eye. Unfortunately, there are a number of surgical problems associated with passing tools, such as the phacoemulsification probe and aspiration needle, through the small anterior chamber of the eye. Moreover, the anterior capsulotomy procedure can disturb other fragile anatomical structures that are anterior to the crystalline lens.

Unlike the anterior capsulotomy, access for a posterior capsulotomy can be obtained using incisions through the sclera on the side of the eye. These incisions do not, in general, affect the refractive properties of the eye like the incisions described above that are made on the cornea or limbus. In addition, there is more operating room on the posterior side of the crystalline lens than the small anterior chamber of the eye. And, in many instances, additional room for tool manipulation can be made on the posterior side of the crystalline lens by performing a partial vitrectomy.

Another advantage of a posterior capsulotomy is that the optical barrier (e.g. the anterior surface of the capsule) is maintained intact during a surgical procedure. Lastly, the use of a posterior capsulotomy can provide flexibility for combining the capsulotomy procedure with other surgical procedures in the back of the eye.

In light of the above, it is an object of the present invention to provide a system and method for performing a posterior capsulotomy.

Another object of the present invention is to provide a system and method for performing a posterior capsulotomy procedure to accommodate the insertion of an Intraocular Lens (IOL) into the lens capsule of an eye.

Still another object of the present invention is to provide a system and method for performing a posterior capsulotomy procedure using laser techniques which is simple to implement and is relatively cost effective.

SUMMARY OF THE INVENTION

In accordance with the present invention, a system and method are provided for inserting an Intraocular Lens (IOL) into the lens capsule of an eye. Specifically, this is accomplished by inserting the IOL through an opening that is created through the posterior capsule of the eye. In overview, the system includes a detector for creating images of the interior of the eye, and it includes a laser unit for generating and focusing a laser beam to a focal point. The system further includes a computer that controls the cooperative functions of the detector and the laser unit.

For an operation of the present invention, the computer processes images that are provided by the detector. Specifically, these images are of tissue inside the eye and their processing by the computer is accomplished to establish an accurate location for the posterior capsule of the eye. As envisioned for the present invention, the detector is preferably an imaging unit that employs imaging techniques selected from a group comprising Optical Coherence Tomography (OCT), Scheimpflug imaging, confocal imaging, two-photon imaging, laser (optical) range finding and acoustical imaging.

In addition to receiving images from the detector, the computer also operates the laser unit to generate and focus a laser beam. In detail, the laser beam is preferably a pulsed laser beam wherein each pulse has a duration less than one millisecond. Furthermore, it is necessary that the energy at the focal point of the laser beam be capable of performing Laser Induced Optical Breakdown (LIOB) of tissue of the posterior capsule.

Based on images of the posterior capsule that have been provided by the detector (imaging unit), the computer is used to control movements of the focal point through tissue of the posterior capsule. As indicated above, this is done for the purpose of performing Laser Induced Optical Breakdown (LIOB) on tissue of the posterior capsule. As envisioned for the present invention, the condition of tissue of the posterior capsule is of interest only insofar as it may affect the laser operation. Stated differently, the present invention pertains regardless whether the posterior capsule is initially intact, or somehow torn. In either case, the intent here is to create an opening through the posterior capsule that can be used for inserting the IOL into the lens capsule. Importantly, in this process, the opening is dimensioned and customized to receive a specific IOL into the lens capsule via the opening.

In accordance with a methodology for the present invention, the crystalline lens of an eye is prepared for its removal from the lens capsule at an appropriate time in the particular procedure. As will be appreciated by the skilled artisan, preparation of the lens can be done in any of several different ways that are well known in the pertinent art. For example, techniques such as hydrodissection and phacoemulsification may be used for this purpose. Preferably, laser techniques such as disclosed in U.S. application Ser. No. 13/436,352, which was filed on Mar. 30, 2012 for an invention entitled "System and Method for Performing Lens Fragmentation," can be useful for this same purpose.

At an appropriate time in the procedure, Laser Induced Optical Breakdown (LIOB) is performed on tissue of the posterior capsule of the eye to create a section of separated tissue. In effect, this involves a laser capsulotomy that creates an opening through the posterior capsule, into the lens capsule of the eye. The section of separated tissue is then removed from the lens capsule to establish the opening. As envisioned for the present invention, this removal of the separated tissue section will be accomplished by first incising the sclera to establish an access port to the vitreous body of the eye. A probe can then be advanced through the access port for engagement of the probe with the section of separated tissue. After the probe has engaged with the separated section of tissue, the separated section of tissue can be removed from the eye by the probe to establish the opening.

Once an opening has been established through the posterior capsule of the eye, the crystalline lens of the eye can be extracted (removed) from the lens capsule of the eye. The extracted lens can then be removed from the eye through the access port that has been created through the sclera. Specifically, this may include removing the whole lens through the scleral incision using mechanical cutters and macelators such as scissors, lassos, guillotine cutters, cautery devices, aqua-jets, ultrasonic blades, a combination of a laser and another extraction device, or any other device or technique sufficient to remove the lens.

Once the crystalline lens has been extracted (removed), an IOL can be introduced through the sclera and inserted through the opening in the posterior capsule to replace the extracted lens. As an additional feature of the present invention, LIOB marks can be established on the lens capsule during the procedure to assist in aligning the IOL in the lens capsule. Such feature may be particularly useful for properly orienting a toric IOL that is to be used for the correction of astigmatism.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
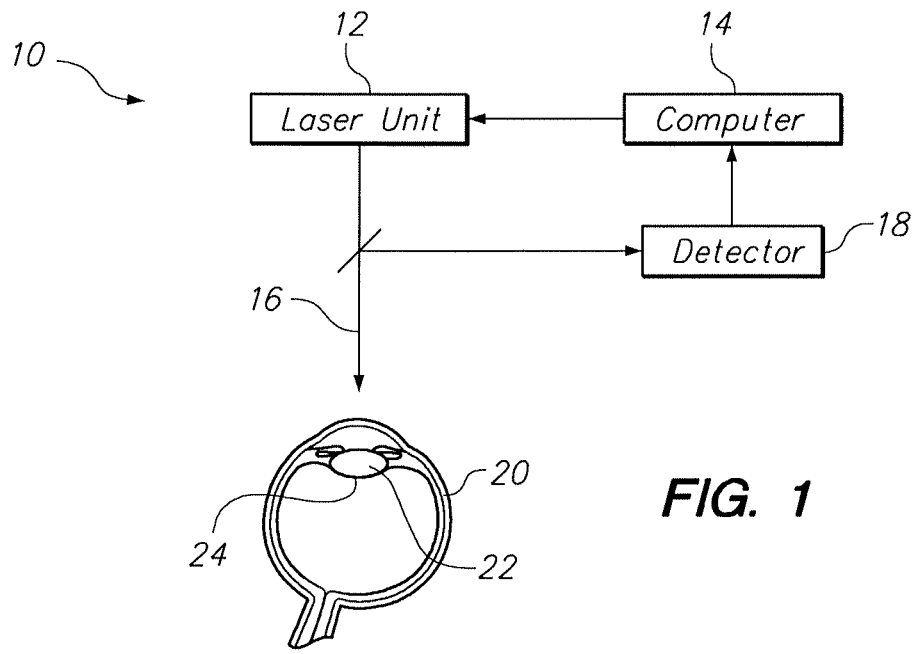
FIG. 1 is a schematic presentation of components for the system of the present invention.

Referring initially to FIG. 1, a system in accordance with the present invention is shown and is generally designated 10. As shown, the system 10 includes a laser unit 12 and a computer 14. As shown, the computer 14 is connected with the laser unit 12 for the purposes of guiding and controlling the movement of a laser beam 16 that is generated and focused by the laser unit 12. Necessarily, the laser unit 12 is of a type that generates a pulsed laser beam 16 which is capable of performing Laser Induced Optical Breakdown (LIOB) on sub-surface anatomical tissue. Preferably, the laser beam 16 will have laser pulses with pulse durations in the femtosecond range.

FIG. 1 also shows that the system 10 can include a detector 18 for creating images of the interior of the eye 20. For example, the detector 18 can include an imaging unit that employs imaging techniques such as Optical Coherence Tomography (OCT), Scheimpflug imaging, confocal imaging, two-photon imaging, laser (optical) range finding and acoustical imaging. As shown, the computer 14 is connected to the detector 18 to receive and process image data from the detector 18 and control the operation of the detector 18. More specifically, images of tissue inside the eye 20 can be processed by the computer 14 to establish an accurate location for the crystalline lens 22 and posterior capsule 24 of the eye 20.

Figure 2A:
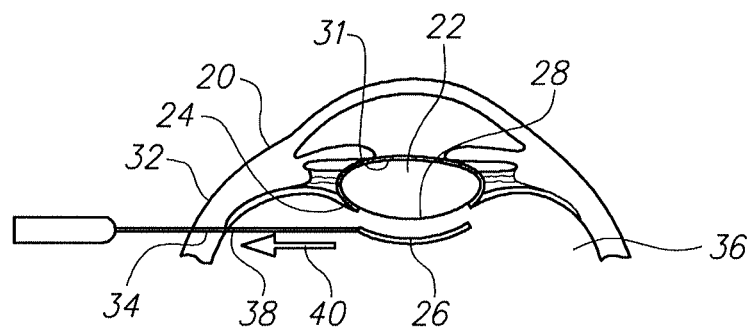
FIG. 2A is a cross section view of the anterior portion of an eye showing the removal of tissue from the posterior capsule of the eye to create an opening into the lens capsule.

FIG. 2A illustrates a procedure for creating a section of separated tissue 26 and removing the tissue 26 from the posterior capsule 24 of the eye 20 to create an opening 28 into the posterior capsule 24. For this procedure, images of the posterior capsule 24 (FIG. 1) are provided by the detector 18 to the computer 14 which uses the image data to control movements of the focal point through tissue of the posterior capsule 24. As this is done, Laser Induced Optical Breakdown (LIOB) occurs on tissue of the posterior capsule 24 to create a section of separated tissue 26. Once the separated tissue is removed, an opening 28 is established through the posterior capsule 24 that can be used for removing the lens 22 and/or inserting an IOL 30 (FIG. 2B) into the lens capsule 31. For this process, the opening 28 can be dimensioned and customized to allow a specific IOL 30 (FIG. 2B) to pass through the opening 28 and be implanted into the lens capsule 31.

Continuing with FIG. 2A, it can be seen that the separated tissue 26 can be removed from the eye 20, by first incising the sclera 32 to establish an access port 34 to the vitreous body 36 of the eye 20. As shown, a probe 38 can then be advanced through the access port 34 for engagement of the probe 38 with the section of separated tissue 26. After the probe 38 has engaged with the separated section of tissue 26, the separated section of tissue 26 can be removed from the eye 20 by the probe 38 (in the direction of arrow 40) and through access port 34 to establish the opening 28. Once an opening 28 has been established through the posterior capsule 24 of the eye 20, as shown, the crystalline lens 22 can be extracted from the lens capsule 31 and removed from the eye 20 through the access port 34.

Figure 2B:
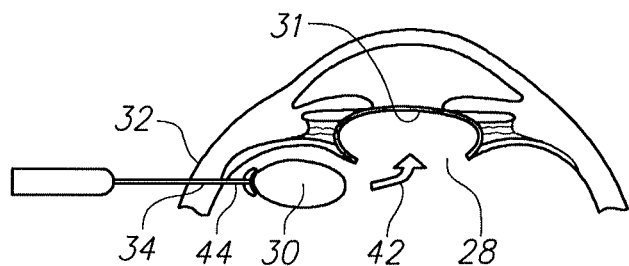
FIG. 2B is a cross section view of the anterior portion of the eye as seen in FIG. 2A, showing the insertion of an Intraocular Lens (IOL) through the opening into the lens capsule of the eye, after the crystalline lens of the eye has been removed from the lens capsule.

FIG. 2B shows that an IOL 30 can be introduced through the access port 34 in the sclera 32 and inserted through the opening 28 (in the direction of arrow 42 and into the lens capsule 31. As shown, probe 44 can be used to place the IOL 30 into the lens capsule 31. As an additional feature of the present invention, LIOB marks (not shown) can be established on the lens capsule 31 during the procedure to assist in aligning the IOL 30 in the lens capsule 31. For example, these LIOB marks may be used to properly orient a toric IOL (not shown) that is to be used for the correction of astigmatism.

While the particular Posterior Capsulotomy Using Laser Techniques as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A system for inserting an Intraocular Lens (IOL) into the lens capsule of the eye comprising:
    a detector for creating images of the interior of the eye;
    a laser unit for generating a laser beam, and for focusing the laser beam to a focal point;
        a computer connected to the detector, and to the laser unit, for processing an image from the detector for use in controlling movements of the focal point to create an opening through tissue of the posterior capsule of an eye for inserting the IOL in the lens capsule of the eye through the opening in the posterior capsule;
    wherein the anterior surface of the capsule is maintained intact during a surgical procedure; and
    wherein the opening is established by creating a section of tissue separated from the posterior capsule, and the system further comprises at least one probe, wherein a probe is advanced through an access port in the sclera to the vitreous body to engage with the section of separated tissue for withdrawal of the separated section of tissue from the eye, and wherein a probe is used to insert the IOL through the access port into the lens capsule.

2. A system as recited in claim 1 wherein the laser beam is a pulsed laser beam.

3. A system as recited in claim 2 wherein each pulse in the pulsed laser beam has a duration less than 1 one millisecond.

4. A system as recited in claim 1 wherein the energy at the focal point of the laser beam is capable of performing Laser Induced Optical Breakdown (LIOB) of the tissue of the posterior capsule.

5. A system as recited in claim 1 wherein the detector is an optical imaging unit.

6. A system as recited in claim 5 wherein the optical imaging unit employs imaging techniques selected from a group comprising Optical Coherence Tomography (OCT), Scheimpflug imaging, confocal imaging, two-photon imaging, laser (optical) range finding and acoustical imaging.

7. A system as recited in claim 1 wherein the opening is dimensioned to receive a specific IOL into the lens capsule via the opening.

8. A non-transitory computer program product for performing ophthalmic surgery inside an eye to create an opening through the posterior capsule of the eye for inserting an Intraocular Lens (IOL) into the lens capsule of the eye, wherein the non-transitory computer program product comprises program sections for respectively:
    processing images from inside the eye, wherein the images are obtained by a detector to establish an accurate location for the posterior capsule of the lens capsule of the eye;
    operating a laser unit in response to images obtained by the detector to generate a laser beam, and to focus the laser beam to a focal point to perform Laser Induced Optical Breakdown (LIOB) on tissue of the posterior capsule;
    controlling movements of the focal point through tissue of the posterior capsule to create an opening through the posterior capsule for use in inserting the IOL into the lens capsule through the opening; and
    establishing LIOB marks on the lens capsule to assist in aligning the IOL in the lens capsule.

* * * * *